United States Patent [19]

Freyre

[11] 4,184,612
[45] Jan. 22, 1980

[54] AUTOMATIC SPRAYER

[76] Inventor: Leopoldo E. Freyre, Jose A. Terry 370, Buenos Aires, Argentina

[21] Appl. No.: 890,284

[22] Filed: Mar. 27, 1978

[30] Foreign Application Priority Data

Mar. 30, 1977 [AR] Argentina ............................. 267031

[51] Int. Cl.² .......................... A61L 9/04; B05B 15/00
[52] U.S. Cl. ...................................... 222/70; 222/174; 222/180; 239/70; 239/274
[58] Field of Search .................... 239/70, 274; 222/70, 222/174, 180

[56] References Cited

U.S. PATENT DOCUMENTS

| | | | |
|---|---|---|---|
| 3,127,060 | 3/1964 | Vosbikian et al. | 222/70 |
| 3,617,214 | 11/1971 | Dolac | 239/274 X |
| 3,680,739 | 8/1972 | Karr | 222/70 |
| 3,737,104 | 6/1973 | Schneider | 239/274 |

FOREIGN PATENT DOCUMENTS

| | | | |
|---|---|---|---|
| 207913 | 8/1976 | Argentina. | |
| 1272507 | 7/1968 | Fed. Rep. of Germany | 239/70 |
| 2515491 | 10/1976 | Fed. Rep. of Germany | 239/70 |

*Primary Examiner*—Robert W. Saifer
*Attorney, Agent, or Firm*—Finnegan, Henderson, Farabow & Garrett

[57] ABSTRACT

Disclosed is a device for emitting an aromatic substance into the surrounding environment which utilizes a pivoted arm carrying a mass as an actuator for an aerosol container containing the aromatic substance and an electronic circuit for maintaining the arm in a position to continue actuation of the aerosol container for a predetermined period of time. In a preferred form, the electronic circuit is such that the arm is controlled to lie in the position maintaining the aerosol container actuated as a function of the elapsed time between succeeding emissions of the aromatic substance.

10 Claims, 6 Drawing Figures

AUTOMATIC SPRAYER

This invention relates to an apparatus for emitting an aromatic substance into the surrounding environment and particularly relates to apparatus for automatically and controllably emitting an aromatic substance into the surrounding environment when actuated over random time intervals, the quantity of which substance emitted upon each actuation being a function of the elapsed time between successive emissions.

In human habitats, for example homes, factories, businesses, offices and the like, there are places or areas, such as bathrooms, pantries, cellars, etc., which have disagreeable air as a result of more or less strong odors. These odors may range between those hardly perceptible to those which are nauseating.

Currently, several types of apparatus are used to alleviate the occurrence of disagreeable odors. For example, flowers which are naturally scented, or slow burning aromatic woods, i.e. sandalwood or incense, or sponges soaked in perfumes which evaporate slowly, or semisolid substances which sublimate at room temperature are frequently located in the spaces normally contained or expected to contain the disagreeable odors. More complicated devices have also been devised. These consist of electrically heated receptacles into which pills of inert substances are placed. These substances are saturated with aromatics which emit their odor slowly by evaporation when the temperature rises above ambient.

All of these above-mentioned devices, however, suffer from one or more drawbacks. For example, they are frequently active at times no disagreeable odors are present and are thus wasteful. Their life is often short-lived requiring frequent renewal, which in turn, causes inconveniene and expense. Also, only a few aromas or perfumes are available and consequently, not all individual tastes can be satisfied. Further, the strength of the aromas is necessarily low-level because the operational principles of each of these apparatus is based on the evaporation of the perfumed substances into the air. Thus, the slowest possible evaporation is sought to increase the operable life of the apparatus. In view of low level strength of the aroma, such apparatus are therefore inadequat when a sudden increase in aromatic intensity is desirable to mask a high level of unpleasant odors even though short-lived, for example in bathrooms. Further, because these apparatus work by evaporation they are inappropriate for storage for appreciable lengths of time because they lose their strength.

In view of the foregoing disadvantages, aerosol ambience deodorizers have been developed. These deodorizers consist of a container filled with a highly perfumed liquid and a gas at low pressure as a vehicle. When the actuator valve was manually pressed, a small cloud or spray of atomizer aerosols, i.e. microscopic drops of the aromatic substance suspended in the air, is emitted. These aerosols are highly advantageous in that only a very small quantity of the extremely concentrated aromatic substances suffices to achieve a desired effect because such substances are in liquid form. Thus, it is possible to achieve a sudden increase in aromatic intensity at any desired time. Of course, after atomization, the aroma slowly disappears but remains sufficiently long at a pleasant high level. Also, because of the extreme concentration of the aromatic substance in liquid form in the aerosol container, the life of the contents of the container is lengthened to allow commercialization at reasonable cost and convenience and long storage or shelf life is achieved. Further, liquid aromatic substances are used, the range of available fragrances is wide enough to satisfy the majority of tastes. For these reasons, aerosol ambience deodorizers are used frequently and their commercialization is presently at a high level. In fact, many companies market deodorizers of this type, competing in various aspects, because of their high development, there is some standardization relating to size of containers and/or contents and/or including fragrances.

This rather well known apparatus, i.e. the aerosol ambience deodorizer, however, suffers from a highly significant drawback in that each such aerosol ambience deodorizer must be manually operated. That is, the operator must take the deodorizer, lift it, point the actuator or release valve to the center of the room, press the button which actuates the valve, calculate or estimate the necessary time of spraying, release the valve actuator button and lastly put the container back. This manual operation has obvious drawbacks. Because of neglect, haste, lack of interest, or forgetfulness, the aerosol may not be used, even when needed and in sight. An objectionable odor may therefore be left in the environment subjecting other individuals to them at subsequent times. Also, for aesthetic reasons as well as reasons that the aerosol container may be removed by an unauthorized individual, the aerosol container is usually kept in closets, chests or alcoves in the area but out of sight of the observer. Therefore, only individuals who have exact knowledge of its storage place can use it and its use by occasional visitors to the area is prevented, even though they may suffer from or cause unpleasant odors. On the other hand, since the container is sometimes within reach of any user, it may give rise to abuse or inadequate use. Also, excessive and unnecessary length of use exhausts the container's contents rather quickly necessitating its replacement.

The present invention provides an apparatus for automatically and controllably emitting an aromatic substance which minimizes or eliminates the foregoing and other problems associated with apparatus for emitting an aromatic substance and provides a novel and improved apparatus for automatically and controllably emitting an aromatic substance having various advantages in construction, operation and use in comparison with such prior apparatus. Particularly, the apparatus of the present invention includes a mechanical device for automatically emitting an aromatic substance with which is judiciously combined electronic and electrical components on a support that is easily attached for example to an access door to the area in which the disagreeable odors exist or are anticipated and can be actuated each time the door is opened or closed to emit a spray of aromatic substance toward the interior of the room. The duration of each emission, i.e. time in which the aroma expands, and consequence of the intensity of its effect, in accordance with the present invention, depends on the previous history of "visits" to the room containing or expected to contain the odor. That is, upon the first actuation, i.e. the first daily visit into such room, the apparatus hereof is actuated a sufficiently long time such that the aromatic substance emitted saturates the atmosphere of the room to a desired level. Of course, the level of the aromatic intensity decreases very slowly with time. When that individual leaves the room, opens and closes the door, the apparatus hereof is once again actuated to dispense or emit the aromatic substance into the room but this time the duration of the emission lasts a much shorter period in time so as to emit only as much additional aromatic subtance as needed to regain saturation.

Wen another individual enters the room, for example immediately after the first individual leaves, this individual finds the ambience or environment nearly saturated with the pleasant odor. Thus, additional aromatic substances will be emitted by the apparatus hereof upon entry by this individual but only for a very brief period of time.

On the other hand, if a longer period of time elapses between succeeding visits to the room such that the intensity of the aromatic substance is very low or disappears, the apparatus of the present invention automatically emits additional aromatic substances for a predetermined time period so that the surrounding environment can once again be saturated with the aromatic substance and the environment returned to a pleasant odor condition. In case the visits to the room follow each other closely with very little time between them, emissions of the aromatic substance upon each visit will, of course, be very small and brief duration, so as to maintain the level of the fragrance but to avoid excessive dispensation of the aroma.

Accordingly, it is a primary object of the present invention to provide a novel and improved apparatus for automatically and controllably emitting an aromatic substance into the surrounding environment.

It is another object of the present invention to provide a novel and improved apparatus for automatically and controllably emitting an aromatic substance into the surrounding environment the duration of each emission being a function of the elapsed time between it and one or more previous emissions.

It is still another object of the present invention to provide a novel and improved apparatus for automatically and controllably emitting an aromatic substance into a surrounding environment which is simple to construct and operate and low in cost.

Additional objects and advantages of the invention will be set forth in part in the description which follows and in part will be obvious from the description, or may be learned by practise of the invention. The objects and advantages of the invention may be realized and attained by means of the instrumentalities and combinations particularly pointed out in the appended claims.

To achieve the foregoing objects and in accordance with the present invention, as embodied and broadly described herein, the apparatus of the present invention includes a support for attachment to a movable member, an arm pivotally carried by said support for movement about a horizontal axis, a stop carried by the arm on one side of its pivotal axis and opposite the actuator of the container containing the substance, means for mounting the container of the support, a predetermined mass carried by the arm on the other side of the pivotal axis and responsive to movement of the member carrying the support to pivot the arm from a first position in which the stop is poised to actuate the actuator into a second position to cause the stop to activate the actuator to emit aromatic substances into the surrounding environment, means carried by the support including an electrical circuit for retaining the arm in the second position to enable continuous actuation of the actuator and emission of the aromatic substance into the surrounding environment over a predetermined period of time, and means enabling the arm to pivot from the second position to the first position after the predetermined time. Preferably, the apparatus includes means for controlling the period of time the arm lies in the second position as a function of the elapsed time between one or more previous emissions of the aromatic substance to control the amount of aromatic substance emitted during the succeeding actuation of the container.

The invention consists in the novel parts constructions, arrangements, combinations and improvements shown and described. The accompanying drawings which are incorporated herein and constitute a part of the specification illustrate several embodiments of the invention and together with the description serve to explain the principles of the invention.

IN THE DRAWINGS

Figure 1:
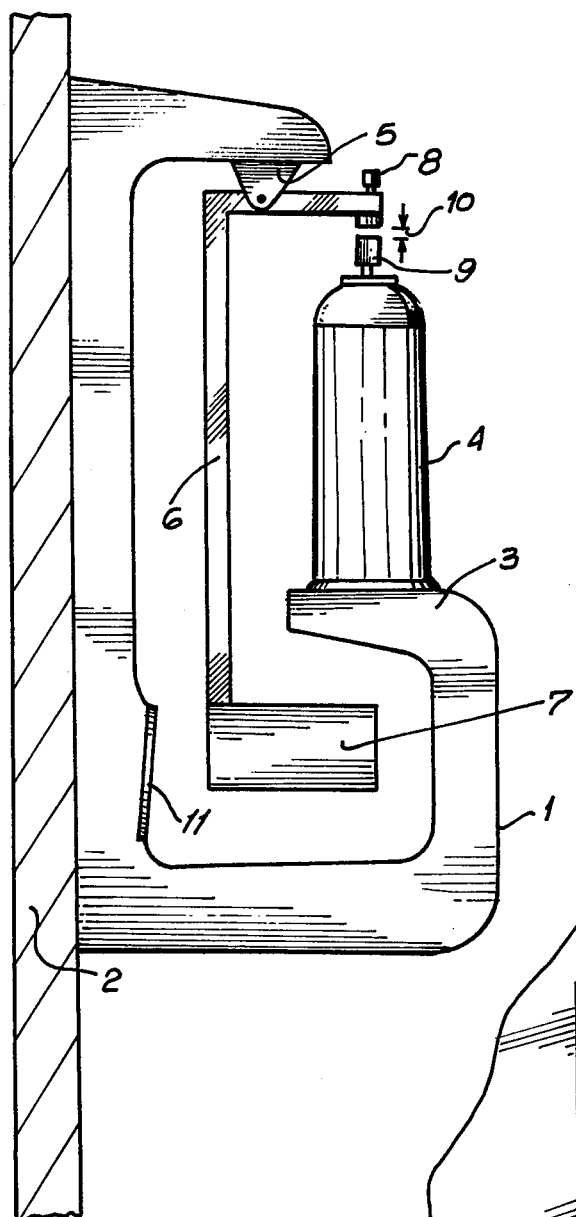
FIG. 1 is a side elevational view illustrating the operational principles of an apparatus constructed in accordance with the present invention, the apparatus being in an inoperative position.

Reference will now be made in detail to the present preferred embodiment of the invention, an example of which is illustrated in the accompanying drawings.

Each of the figures uses the same reference numerals for like parts. The apparatus hereof is illustrated in FIG. 1, and includes a support 1, which may be attached to one side of movable member or door 2, for example at the upper corner near the door jamb as illustrated in FIG. 2.

A seat 3 is formed in support 1 and it holds a container 4 containing aromatic substances in liquid form, the container including an actuator, i.e. an atomizer actuated by a mechanical means or similar actuating means. In addition to this support, the apparatus is provided with a hinge 5 for a pendulum structure formed by an arm 6 which has, at its bottom, a mass 7 and at its top an adjustable stop 8 opposite valve 9 which actuates container 4.

Figure 2:
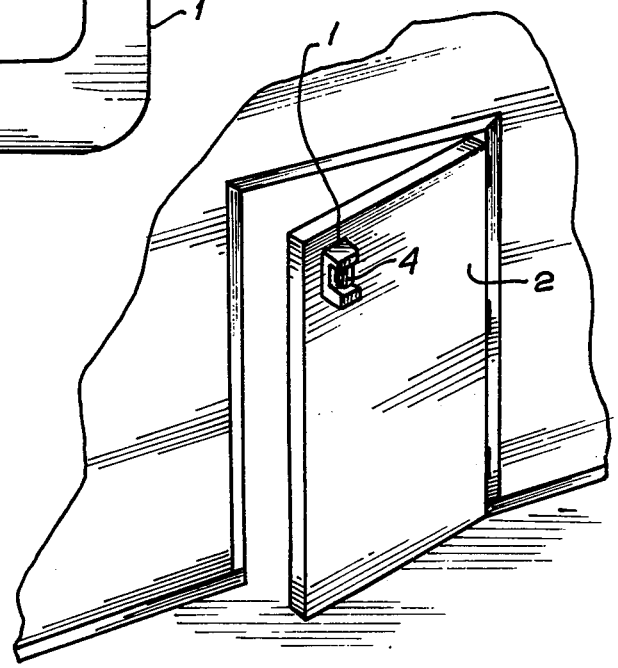
FIG. 2 is a perspective view of the apparatus hereof installed behind a door.

The shaft of hinge 5 is located in such manner that in its rest position, shown in FIG. 1, the center of gravity of the pendulum structure is in the vertical line passing through said shaft, defining the position illustrated in FIG. 1 for the above mentioned pendulum structure when the door is not moved, thus allowing adjustment of stop 8 to create a small gap 10 between it and the actuator as shown in the FIG. 1.

Figure 3:
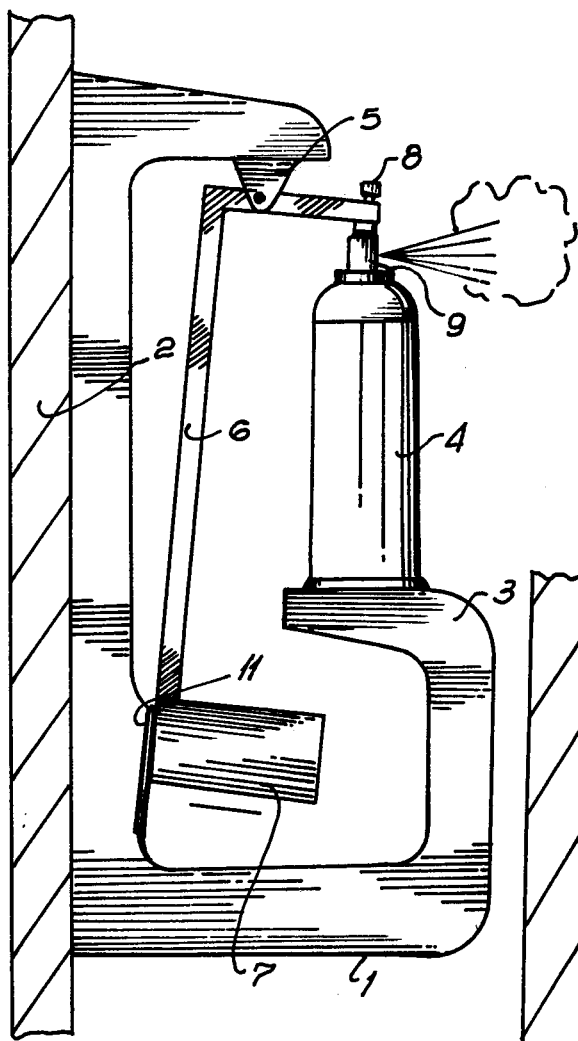
FIG. 3 is a view similar to FIG. 1 but illustrating the apparatus of the invention in its operative position.
Figure 4:
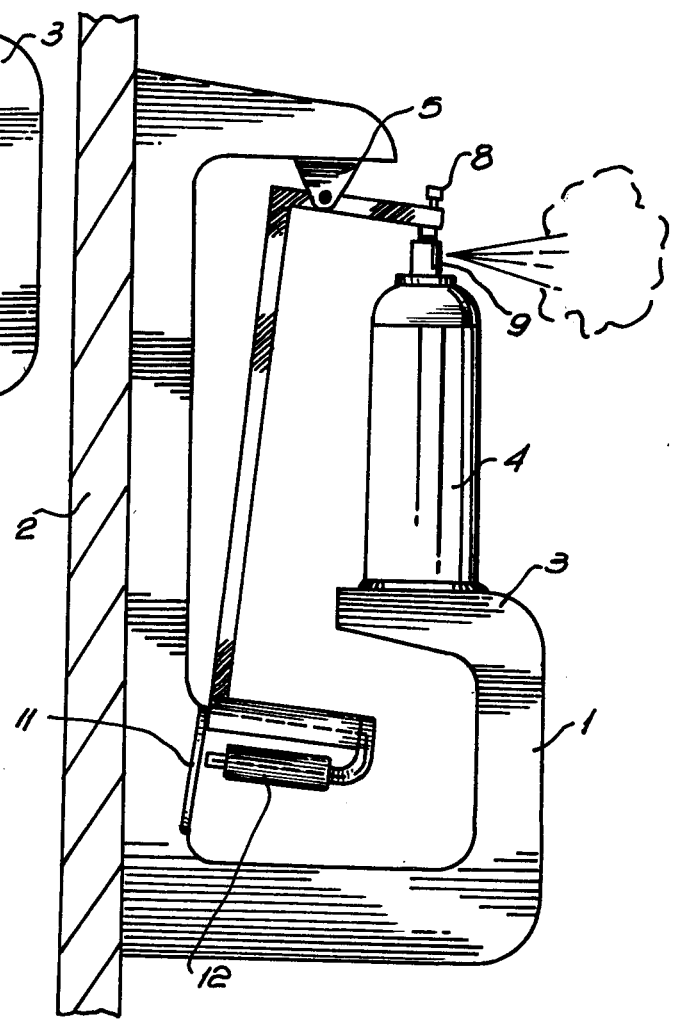
FIG. 4 is a view similar to FIG. 1 illustrating an electromagnetic component of the apparatus of the invention.

When the door is opened, because of inertia, the mass tends to remain in its place with respect to ground (earth). But in the meantime, the apparatus attached to the door has been displaced, for example to the right. This gives rise to a movement of the pendulum structure with respect to support 1 to the left, until it touches stop 11 forming the lower part of support 1. As shown in FIG. 3, this causes the actuation of the release valve of the aerosol, whereby a cloud of aromatic substance is sprayed into the room.

Up to this point, these figures explain in simplified manner the origin of the energy actuating the aerosol release valve. As can be seen, the inertia of the mass provided by the force exerted by the opening movement of the door is thus used to activate the aerosol container.

In accordance with the present invention, means are provided for retaining the arm in the position illustrated in FIG. 3 to enable continuous actuation of the actuator and emission of the aromatic substance into the surrounding environment over a predetermined period of time and for returning the arm to its inoperative position after the period of time has elapsed. Without such means, control of the aromatic substance emission time cannot be obtained because the aerosol is otherwise actuated for a time which is equal to the half-period of oscillation of the suspended structure. This length of time is approximately constant and is very short, i.e. a fraction of a second, if the apparatus is of typical dimensions. Therefore it is necessary to provide an auxiliary system so that once the pendulum structure is actuated and activates the aerosol to emit the aromatic substance, it remains in that position, i.e. an inclined pendulum, during a predetermined length of time to emit the required amount of aromatic substance. Preferably this "latching" time is also adjustable and is varied with the "previous history" of the visits to the room.

As embodied, this means comprises an electronic, electromagnetic system illustrated in FIG. 4, that is preferably integrated into the apparatus of the invention.

In FIG. 4, part of mass 7 is replaced by an electromagnet 12 formed of a material which supplies an inertial mass equal to the mass replaced. The pole faces of the electromagnet are so made as to perfectly rest against the surface of stop 11 which must be made of a ferromagnetic material.

If by a suitable means the coil of the electromagnetic device is energized coincidentally with the actuation of the suspended structure, it will latch to the ferromagnetic stop 11 when reaching it because of the magnetic attraction.

By maintaining the electric current, the process of emitting the aromatic substance may thus be continued for the desired time. This emission will stop only when the current is cut, at which time the pendulum structure is unlatched for return to its rest position.

In order to further describe the operation of the apparatus, reference is made to FIG. 5 which is a section of a preferred embodiment of the invention.

In FIG. 5, arm 6 of the pendulum structure is formed as a housing for an electric power source consisting of a set of batteries 13. Also a third stop 14, which dampens and receives the impact of the return of arm 6, is placed on support 1.

Mass 7 in FIG. 4 includes an electromagnet formed by a core 15 formed of soft iron, on which is wound an excitation coil 16, said electromagnet having pole pieces made of soft iron for guiding the magnetic flux 17, as shown by dashed lines in FIG. 5 and the corresponding arrows.

A counterweight 18 permits integrating the inertial mass which is required for the functioning of the apparatus if the mass corresponding to that of the components proper, of the arm and of the electromagnet, is insufficient, the electromagnet being mounted on the arm by a bracket 19, which is made of a non-magnetic material.

In accordance with the invention means are provided for controlling the period of time the arm stays in its operative position as a function of the elapsed time between one or more previous emissions of the aromatic substance to control the amount of aromatic substance emitted during the succeeding actuation of the container. As embodied, this means comprises a printed circuit 20 on which are mounted the corresponding electronics of the actuating circuit and the control of the electromagnet. This circuit includes a potentiometer 22, or variable resistance, which may be adjusted externally by screw 21, for example by introducing the tip of a screwdriver or another appropriate tool through an appropriate aperture 23 made in support 1. When the wiper of this potentiometer is moved or varied, because of its connection to appropriate points in the electronic circuit, the effective time of aromatic substance emission will vary as a function of the previous history of entries and exits into and from the room, thus permitting operation of the unit for either small or large rooms with more or less ventilation, or for different tastes of the owners, for reasons of maximum savings in aromatics, for more or less aromatic intensity, etc.

Reference numeral 31 denotes a mercury switch enclosed in a tube formed of glass or other material. The output electrodes from mercury switch 31 are connected to appropriate points of the printed circuit. The location of this mercury switch is such that for the rest condition (door closed, or not moving), and because of gravity, the mercury remains at rest in the tube in the area opposite the contacts to maintain the switch in an open condition. When the door is opened, inertia causes the arm to move to the left as seen in FIG. 5 to actuate the aerosol. The mercury is also displaced toward the area of the electrodes, contacts the electrodes and closes the electrical circuit connected to the switch. Closing the circuit between those electrodes initiates the supply of power to the electromagnet coil so that the core adheres to the ferromagnetic stop 11 and the arm remains inclined to the left to continue and maintain the emission of the aromatic substance into the surrounding environment. After a given period of time, depending on the previous history of entries and exits into the room, current is cut off, the electromagnet will unlatch from stop 11 and arm 6 returns to the position illustrated in FIG. 5 discontinuing the emission of the aerosol.

This is achieved by a particular electronic circuit for control and time delay which is described below in relation to FIG. 6.

This circuit includes a power supply provided by batteries 13, a semiconductor diode 14, the excitation coil 16, the mercury switch 31, a type NPN transistor 25, another type PNP transistor 26, a capacitor 32, a potentiometer 22, and the resistors 27, 28, 29, and 30.

Coil 16 is coupled to the collector of transistor 25 and the series combination of coil 16 and the collector-emitter path of transistor 25 is coupled across the output terminals of batteries 13. Diode 14 is in parallel connection with coil 16. The base of transistor 25 is coupled to the positive terminal of batteries 13 through the series combination of resistor 29, resistor 30 and mercury switch 31. The emitter-collector path of transistor 26 is coupled in parallel with the series combination of mercury switch 31 and resistor 30 while the base of transistor 26 is coupled to the junction between coil 16 and the collector of transistor 25 by the series combination of capacitor 32, potentiometer 22 and resistor 27. Resistor 28 is connected in parallel across capacitor 32.

Figure 6:
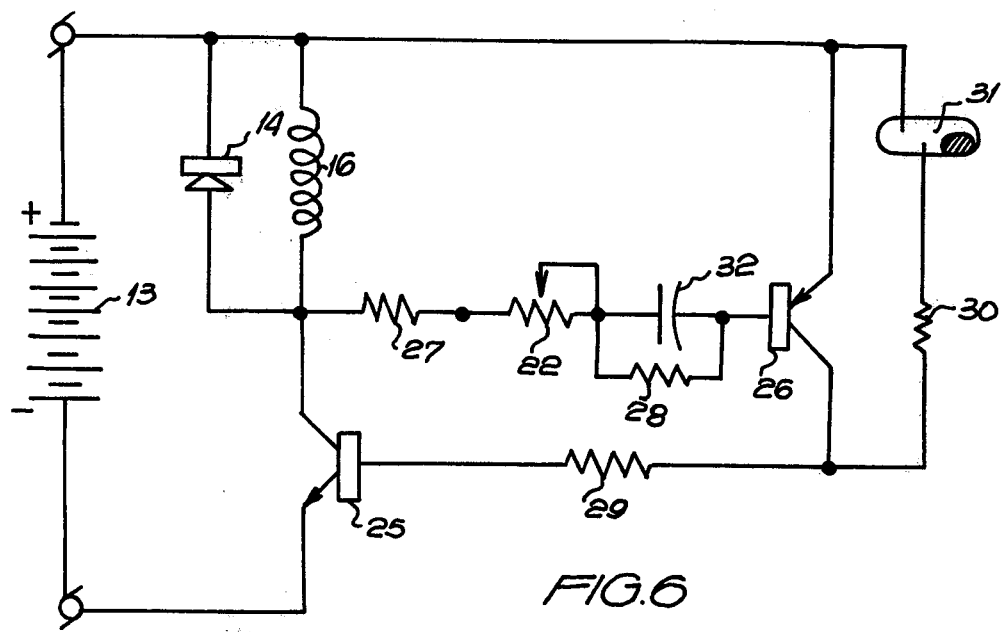
FIG. 6 is a schematic of an electronic circuit for use in the apparatus of the present invention.

The operation of the circuit will now be described. With the door to the room closed or motionless, mercury switch 31 is open and the drop of mercury rests in the area opposite the electrodes of switch 31, as shown in FIG. 6. Nothing significant happens in the circuit at this time because both transistors 25 and 26 are open and cannot conduct current. Thus, in the rest condition, no current at all passes from the batteries to the circuit except a minute leakage current in transistor 25. Because there is no current, the life of the batteries is greatly extended.

Figure 5:
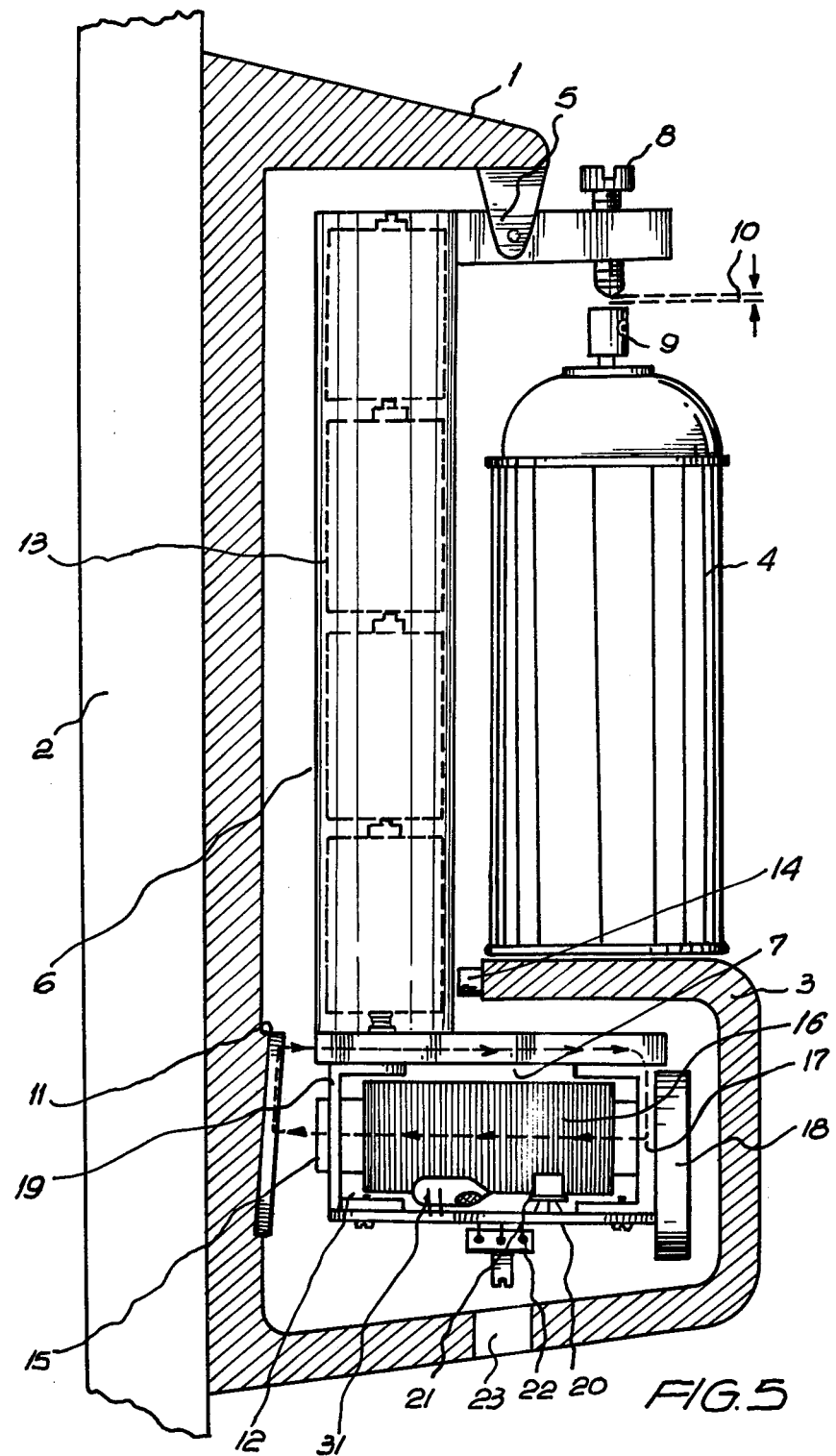
FIG. 5 is side elevational view of a preferred apparatus of the invention.

Now assume that the door is opened for the first time. Because of the functioning arm 6, it swings and the valve 9 for the aerosol is actuated. Simultaneously the mercury drop in switch 31 is displaced and closes the circuit between the electrodes. Because the drop recoils after hitting the end of the tube of switch 31 housing the drop, current from the base of transistor 25 may circulate for an instant through resistors 29 and 30 in series connection with the base of transistor 25 and mercury switch 31. When there is a current in the base of transistor 25, there is conduction in the collector-emitter circuit of transistor 25 which provides a current to the coil 16 which then latches the core 15 against the ferromagnetic stop 11 (FIG. 5), maintaining the emission of the aerosol independently of the period of mechanical oscillation of the pendulum structure.

The current in transistor 25 and through resistors 29 and 30 and switch 31 is cut a moment later because switch 31 opens upon recoil of the mercury drop. To prevent cutting the current through transistor 25 and termination of system operation, transistor 26 and its associated circuit start functioning. When power is initially supplied to coil 16, the voltage from batteries 13 appears across the coil terminals, less a small fraction of a volt which represents the voltage drop across the collector and emitter of transistor 25. This voltage across coil 16 is applied in the circuit to the base transistor 26 through resistors 27, 22 and 28.

Initially, the capacitor 32 was totally discharged, for which reason there may circulate through transistor 26 a charging current for capacitor 32 through resistor 27 in series with variable resistor 22; the current shunted by resistor 28 being negligible on account of a high value of resistor 28.

When current passes through the base of transistor 26, transistor 26 becomes conducting in its collector-emitter circuit and is thus capable of delivering current to the base of transistor 25 through resistor 29 independently of the state of conduction through mercury switch 31, i.e. when the drop has already recoiled. Thus, the power supply to coil 16 is maintained and the emission of aerosol continues.

Capacitor 32, however, continues charging through resistors 27 and 22 by means of a gradually decreasing current according to the exponential law or time constant of charging RC circuits.

As time passes, i.e. after a few seconds, the current through transistor 26 becomes too small to keep transistor 25 energized at which time the current through transistor 25 is cut. This deenergizes coil 16 which permits the arm 6 to return to its initial position and stops the aerosol emission.

From this time on, the system remains at rest electrically and mechanically, except that during this rest period, the electrical charge on capacitor 32 is slowly dissipated through fixed resistor 28 in parallel with capacitor 32.

After a predetermined length of time, namely several time constants of the circuit comprising resistor 28 and capacitor 32, capacitor 32 is effectively completely discharged. If the door is once again opened after that time, aerosol will be emitted for several seconds, exactly as in the previous case. If, however, the door is opened before capacitor 32 is completely discharged, the new charging process through resistors 27 and 22 will last a period of time less than in the previous case. Consequently, coil 16 is energized for a shorter period of time and the aerosol emission time likewise is shorter.

The aromatic substance discharges therefore will gradually become shorter when less time has elapsed between actuations. In the limiting case, when an actuation occurs immediately after the prior one, the emission of aerosol lasts only a small fraction of a second, practically coinciding with the half period of oscillation of the pendulum structure. Consequently, it can be seen that the period of time the arm 6 is in a position causing continuous emission of the aerosol substance is a function of the elapsed time between succeeding emissions of the aromatic substance.

This particular functioning is called the memory of the previous history of actuations. By this mechanism, a pleasant and noncounterproductive effect, i.e. excess of ambience saturation is achieved. Further, this also provides for long lived aromatic substances with consequent saving and ease of operation, that is, less frequent need to change the aerosol components.

The potentiometer 22 integrated into the charging circuit 32 thus affects the real time of operation for a given history, thus permitting adjustment of the apparatus to different-sized rooms and/or other particulars.

Resistance 28, which is high, must be chosen to obtain the greatest possible savings in aerosol, while allowing satisfactory operation for normal ambiences.

The diode 14 in parallel with coil 16 is for shunting extra-high break voltages which originate in the highly inductive circuit of coil 16 and which might damage transistors 25 and 26.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. Apparatus for automatically and controllably emitting an aromatic substance into the surrounding environment from a container containing the substance and having an actuator for emitting the substance comprising:

a support for attachment to a movable member,
an arm pivotally carried by said support for movement about a generally horizontal axis,
a stop carried by said arm on one side of its pivotal axis and located opposite the actuator of the container containing the substance,
means for mounting said container on said support,
a mass carried by said arm on the other side of said pivotal axis and responsive to movement of the member to which the support is attached to pivot said arm from a first, inoperative position to a second operative position that causes said stop to actuate the actuator and emit aromatic substance into the surrounding environment, means carried by said support including an electrical circuit for retaining said arm in said second position to enable continuous actuation of the actuator and emission of the aromatic substance into the surrounding environment over a predetermined period of time and for permitting said arm to return to said first position after said predetermined period of time.

2. Apparatus according to claim 1 in combination with said container in which said container comprises an aerosol can and the actuator is a pushbutton valve carried by said container.

3. Apparatus according to claim 1 wherein the emission of the aromatic substance is repeatable in time, and means are provided for controlling the period of time said arm lies in said second operative position as a function of the elapsed time between one or more previous emissions of the aromatic substance to control the amount of aromatic substance emitted during the succeeding actuation of the container.

4. Apparatus according to claim 1 wherein said electrical circuit includes an electromagnet carried by one of said arm and said support and a stop formed of magnetic material carried by the other of said arm and said stop, and a switching circuit electrically coupled to said electromagnet for energizing the electromagnet to hold said arm in said second position for said predetermined period of time and for deenergizing said electromagnet to enable the arm to move toward said first position at the end of said predetermined time.

5. Apparatus according to claim 4 wherein said switching circuit includes an element having an exponential time constant.

6. Apparatus according to claim 4 wherein said electrical circuit includes a motion responsive switch for activating said switching circuit.

7. Apparatus according to claim 6 wherein said electrical circuit comprises first circuit means responsive to said motion responsive switch for activating said switching circuit.

8. Apparatus according to claim 7 wherein said electrical circuit further includes second circuit means responsive to initial operation of said first circuit means for maintaining operation of said first circuit means beyond said initial operation of said first circuit means.

9. Apparatus according to claim 8 wherein said second circuit means comprises an RC timing network to control the duration of operation of said first circuit means beyond said initial operation.

10. Apparatus according to claim 1 wherein said electrical circuit comprises a power source, a motion sensitive switch, a first transistor, a second transistor and an RC network, and circuit means for completing a current path from said power source to said actuator through said first transistor upon actuation of said motion sensitive switch and means for maintaining said current path upon deactivation of said motion sensitive switch by shunting said motion sensitive switch with said second transistor for a period of time established by said RC network.

* * * * *